US012620817B2

(12) United States Patent
Wimmer et al.

(10) Patent No.: US 12,620,817 B2
(45) Date of Patent: May 5, 2026

(54) MEDICAL DEVICE WITH IMPROVED BATTERY STORAGE SYSTEM

(71) Applicant: Siemens Healthineers AG, Forchheim (DE)

(72) Inventors: Michael Wimmer, Weisendorf (DE); Josef Deuringer, Herzogenaurach (DE); Karsten Kruschat, Nuremberg (DE); Andreas Boehme, Nuremberg (DE); Jonas Geyer-Ramsteck, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 19/076,371

(22) Filed: Mar. 11, 2025

(65) Prior Publication Data

US 2025/0293531 A1 Sep. 18, 2025

(30) Foreign Application Priority Data

Mar. 13, 2024 (DE) .................... 10 2024 202 352.3

(51) Int. Cl.
*H02J 7/00* (2006.01)
*A61B 6/00* (2024.01)
(Continued)

(52) U.S. Cl.
CPC ......... *H02J 7/0016* (2013.01); *H01M 10/425* (2013.01); *H02J 1/084* (2020.01);
(Continued)

(58) Field of Classification Search
CPC ...... H02J 7/0016; H02J 7/00032; H02J 1/084; H02J 7/00712; H02J 7/342; H01M 10/425;
(Continued)

(56) References Cited

U.S. PATENT DOCUMENTS 10,879,717 B2 * 12/2020 Yang ..................... H02J 7/0048
2009/0027006 A1 1/2009 Vezzini et al.
(Continued)

FOREIGN PATENT DOCUMENTS

| CH | 715078 A2 | 12/2019 |
|---|---|---|
| CN | 103918153 A | 7/2014 |
| DE | 102020209450 A1 | 1/2022 |

OTHER PUBLICATIONS

German Office Action and English translation thereof for German Application No. 10 2024 202 352.3 mailed Jan. 20, 2025.
(Continued)

*Primary Examiner* — Carlos Amaya
(74) *Attorney, Agent, or Firm* — Harness, Dickey & Pierce, P.L.C.

(57) ABSTRACT

A medical device includes an electric battery storage system including a plurality of battery modules; module fixtures, wherein the battery modules are in the module fixtures, an arrangement of the battery modules in the module fixtures provide a power-related interconnection of the battery modules, the module fixtures are divided into a plurality of basic fixtures and at least one additional fixture; and an equalizing arrangement assigned to the battery storage system, the equalizing arrangement being configured to equalize a low-loss equalization of a basic charge level and an additional charge level between battery modules in the basic fixtures and having a uniform basic charge level and a battery module in the additional fixture and having an additional charge level, and the equalizing arrangement is not configured to cause a uniform basic charge level within the battery modules in the basic fixtures.

15 Claims, 4 Drawing Sheets

(51) Int. Cl.
    *H01M 10/42*     (2006.01)
    *H02J 1/08*     (2006.01)
    *H02J 7/34*     (2006.01)

(52) U.S. Cl.
    CPC ...... *H02J 7/00032* (2020.01); *H02J 7/00712*
    (2020.01); *H02J 7/342* (2020.01); *A61B 6/56*
    (2013.01); *H01M 2010/4271* (2013.01); *H01M*
    *2010/4278* (2013.01)

(58) Field of Classification Search
    CPC .. H01M 2010/4271; H01M 2010/4278; A61B
    6/56
    See application file for complete search history.

(56)              References Cited

U.S. PATENT DOCUMENTS

| | | | |
|---|---|---|---|
| 2011/0156620 A1* | 6/2011 | Yeh | H02J 7/1492 |
| | | | 307/10.7 |
| 2014/0145681 A1 | 5/2014 | Vuorilehto et al. | |
| 2017/0163060 A1 | 6/2017 | Zheng et al. | |
| 2019/0044336 A1 | 2/2019 | Wagner et al. | |
| 2019/0288520 A1 | 9/2019 | Abdel-Monem et al. | |
| 2022/0242244 A1* | 8/2022 | Clay | H01M 10/425 |

OTHER PUBLICATIONS

German Decision to Grant and English translation thereof for German Application No. 10 2024 202 352.3 mailed May 27, 2025.

* cited by examiner

MEDICAL DEVICE WITH IMPROVED BATTERY STORAGE SYSTEM

CROSS-REFERENCE TO RELATED APPLICATION(S)

The present application claims priority under 35 U.S.C. § 119 to German Patent Application No. 10 2024 202 352.3, filed Mar. 13, 2024, the entire contents of which is incorporated herein by reference.

FIELD

One or more example embodiments is based on a medical device with an improved battery storage system.

RELATED ART

A typical example of a medical device is an X-ray system. Such a system is customarily fed from a supply network. During ongoing operation, however, its power consumption fluctuates significantly. During phases with high power consumption (power phases), the battery storage system can therefore supply energy to the medical device, which is fed back to the battery storage system from the supply network during phases with low power consumption (power pauses). This allows the power consumption from the supply network to be evened out and the maximum power consumption from the supply network to be reduced or even significantly reduced. If need be, autarkic operation of a mobile medical device independently of the mains supply is also possible. Depending on the situation, the battery storage system may therefore be essential for the ongoing operation of the medical device. If it is essential, only the battery storage system enables the ongoing operation of the medical device. If it is not essential, the battery storage system supports ongoing operation, for example by reducing the maximum power consumption from the supply network. Alternatively or in addition, the battery storage system can enable the ongoing operation or emergency operation of the medical device for a limited time in the event of failure of the supply network. The extent to which ongoing operation or emergency operation is enabled is determined by the energy requirement of the medical device and the design of the energy storage system.

In the prior art, the battery storage system customarily consists of a plurality of battery modules which are connected in parallel and in series as required in order to meet the requirements of the respective system. Often the individual battery modules are designed in such a way that handling of the individual battery modules by service technicians who are not specifically qualified is also permitted in the legal sense. As a result, such persons may also replace modules.

When the battery storage system is installed for the first time, all of the battery modules customarily have the same charge level. During subsequent operation, all of the modules continue to have the same charge level as a rule. However, the charge level can be any value between a minimum value and a maximum value—in an extreme case between 0% (=fully discharged) and 100% (=fully charged).

If an individual battery module fails or otherwise no longer meets the required specification, in some cases the entire battery storage system is replaced and disposed of. This is disadvantageous because, as a rule, the other battery modules still work properly. Excessive costs are therefore incurred. Resources are also consumed unnecessarily.

From the basic approach, it is known and also readily conceivable to replace only a single battery module. Here the problem arises, however, that the newly installed battery module may have a different charge level from the battery modules already in the device. For example, due to applicable hazardous goods guidelines, newly manufactured battery modules are usually stored and transported with a maximum charge level of approx. 30%. However, the charge level of the battery modules already in the device may have a different value, possibly even a significantly different value. However, in order to be able to operate the medical device to its full extent, all of the battery modules must have (at least essentially) the same charge level.

Passive balancing circuits are known in the prior art. Such balancing circuits are used in the prior art inside the respective battery modules in order to equalize the charge levels between the individual battery cells of a respective battery module. It is conceivable to also use such passive balancing circuits for balancing the charge levels of the battery modules. However, this is disadvantageous. Firstly, such equalization of the charge levels requires a considerable amount of time, as a rule several hours. Furthermore, the charge levels in passive balancing circuits are equalized by balancing charge differences through current flow via resistors, so that the energy is converted into heat and thus losses occur.

Furthermore, active balancing circuits are also known in the prior art. Such balancing circuits are also used in the prior art to equalize charge levels. It is conceivable to also use such active balancing circuits for balancing the charge level of the battery modules. Due to the relatively large number of battery modules, however, a high number of active balancing circuits would be required. This solution is therefore not adopted for reasons of cost.

SUMMARY

One or more example embodiments creates possibilities via which, even when replacing an individual battery module, a low-loss equalization of the charge level of this battery module with the charge levels of the other battery modules is possible in a simple and cost-efficient manner.

BRIEF DESCRIPTION OF THE DRAWINGS

The properties, features and advantages described above and the manner in which they are achieved will become clearer and more comprehensible in connection with the following description of the exemplary embodiments, which will be explained in more detail in connection with the drawings. The following diagrammatic view shows.

DETAILED DESCRIPTION

Figure 1:
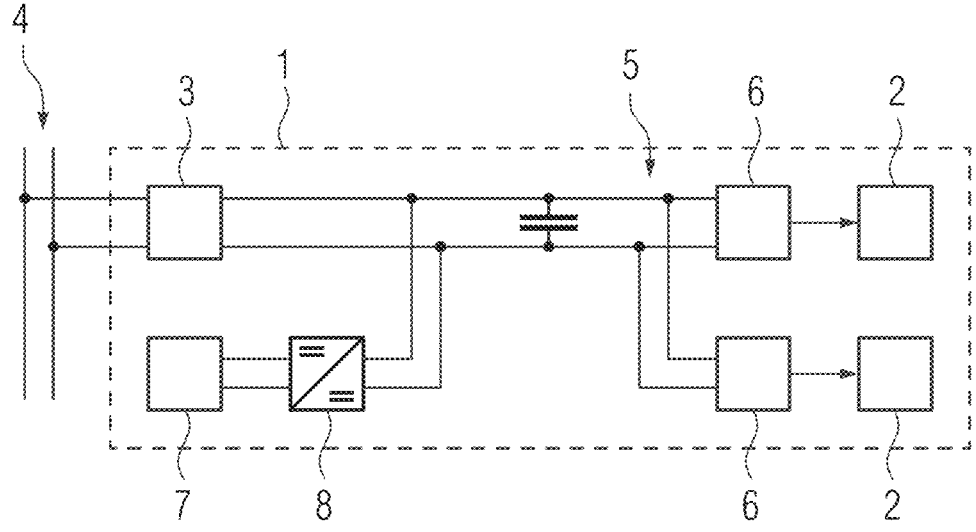
FIG. 1 illustrates a medical device according to one or more example embodiments.

According to one or more example embodiments, a medical device of the type mentioned at the outset is designed in such a way that the module fixtures are divided into a plurality of
basic fixtures and at least one additional fixture,
that an equalizing arrangement is assigned to the battery
storage system,
that the equalizing arrangement is capable of effecting a
low-loss equalization of the basic charge level and the
additional charge level between battery modules
arranged in the basic fixtures having a uniform charge
level on the one hand and a battery module arranged in
the additional fixture and having an additional charge
level on the other hand,
that conversely the equalizing arrangement is not capable
of bringing about a uniform basic charge level within
the battery modules arranged in the basic fixtures.

The modular design of the battery storage system simpli-
fies the replacement of battery modules. The division of the
module fixtures into basic fixtures and theoretically at least
one, in practice usually precisely one, additional fixture
makes it possible to introduce a new battery module into the
network of battery modules at a defined point. The equal-
izing arrangement enables the low-loss equalization of the
charge levels. As it is known in which module fixture the
new battery module is arranged (namely in the additional
fixture), and furthermore the new battery module is the only
battery module whose charge level may deviate from the
uniform charge level of the other battery modules, the
equalizing arrangement can be designed very simply. This is
because, when designing the equalizing arrangement, it is
not necessary to consider the possibility that the new battery
module could be in any module fixture of the medical
device.

For example, it is possible that the battery modules
arranged in the module fixtures are connected by a data-
related interconnection to a battery management system of
the medical device, so that the battery modules arranged in
the module fixtures can transmit their respective charge level
to the battery management system, and that the basic fixtures
are assigned a basic charging device which spans the basic
fixtures, via which the uniform basic charge level of the
battery modules arranged in the basic fixtures can be
changed without influencing the additional charge level of
the battery module arranged in the additional fixture.

In this case, the battery management system, which is
customarily present anyway, can, via communication with
the battery modules arranged in the module fixtures, detect
or query their charge levels and if necessary, adjust the
uniform basic charge level of the battery modules arranged
in the basic fixtures to the additional charge level of the
battery module arranged in the additional fixture.

In this context, it is particularly preferable if, in order to
adapt the uniform basic charge level of the battery modules
arranged in the basic fixtures to the additional charge level
of the battery module arranged in the additional fixture
during ongoing operation of the medical device, the battery
modules arranged in the basic fixtures are discharged or
electrical energy is supplied to the battery modules arranged
in the basic fixtures in the same manner as if no battery
module were arranged in the additional fixture. This is
because then the adjustment takes place all by itself without
any further special measures. Only the additional charge
level needs to be known. Which of the two measures—
discharging the battery modules arranged in the basic fix-
tures or supplying electrical energy to the battery modules
arranged in the basic fixtures—is taken, depends on whether
the additional charge level is higher or lower than the basic
charge level.

Emergency operation is when the external electrical
energy supply of the medical device has failed. During
emergency operation of the medical device, the battery
modules can therefore not be charged. However, in the event
that it is necessary to discharge the battery modules arranged
in the basic fixtures in order to adapt the uniform basic
charge level of the battery modules arranged in the basic
fixtures to the additional charge level of the battery module
arranged in the additional fixture, in this case too, discharg-
ing can take place in the same manner as if no battery
module were arranged in the additional fixture.

This approach is particularly advantageous if the battery
module arranged in the additional fixture is not involved in
the ongoing operation or emergency operation of the medi-
cal device.

Alternatively or in addition to the basic charging device,
it is possible that the additional fixture is proprietarily
assigned to an additional charging device via which the
additional charge level of the battery module arranged in the
additional fixture can be changed without influencing the
uniform basic charge level of the battery modules arranged
in the basic fixtures. In this case, the battery management
system can—alternatively or in addition to adjusting the
uniform basic charge level of the battery modules arranged
in the basic fixtures to the additional charge level of the
battery module arranged in the additional fixture—also
adjust the additional charge level of the battery module
arranged in the additional fixture to the uniform basic charge
level of the battery modules arranged in the basic fixtures.

The latter approach can be taken with or without involv-
ing the battery module arranged in the additional fixture in
the ongoing operation or the emergency operation of the
medical device. The only requirement is a dedicated charg-
ing option for the battery module concerned.

Another possibility is for the battery storage system to be
assigned an active balancing circuit via which charge can be
transferred with low loss between all of the battery modules
arranged in the basic fixtures on the one hand and the battery
module arranged in the additional fixture on the other hand,
and for the change in the additional charge level of the
battery module arranged in the additional fixture to be
distributed evenly across the battery modules arranged in the
basic fixtures.

In this case, the adjustment of the uniform basic charge
level and the additional charge level to one another is simply
carried out by the active balancing circuit without the
involvement of a battery management system. The active
balancing circuit is designed in such a way that the existing
"imbalance" between the plurality of battery modules
arranged in the basic fixtures and the individual battery
module arranged in the additional fixture ("many against
one") is taken into account accordingly. For example, the
correspondingly higher voltage can be taken into account
when the battery modules arranged in the basic fixtures are
connected in series.

As already mentioned, it is alternatively possible that the
battery module arranged in the additional fixture is involved
or is not involved in the ongoing operation or emergency
operation of the medical device. If it is not involved,
electrical energy is taken from the battery modules arranged
in the basic fixtures during ongoing operation and/or during
emergency operation of the medical device in order to
operate the medical device, but not from the battery module
arranged in the additional fixture. If it is involved, electrical
energy is drawn both from the battery modules arranged in
the basic fixtures and from the battery module arranged in the additional fixture during ongoing operation and/or during emergency operation of the medical device in order to operate the medical device.

It is even possible that a switching facility is assigned to the battery storage system, via which it is possible to dynamically adjust whether electrical energy is drawn exclusively from the battery modules arranged in the basic fixtures or both from the battery modules arranged in the basic fixtures and from the battery module arranged in the additional fixture during ongoing operation and/or during emergency operation of the medical device in order to operate the medical device. In this case, in particular, equalization of the charge levels with one another can take place while the battery module arranged in the additional fixture is not involved in the ongoing operation or emergency operation of the medical device. After equalization of the charge levels, the battery module arranged in the additional fixture can then be involved in the ongoing operation or emergency operation of the medical device by actuating the switching facility.

The battery storage system is preferably designed in such a way that it supports and/or enables the ongoing operation of the medical device and/or enables the emergency operation of the medical device as long as a number of basic fixtures in which no battery module is arranged or in which the battery module arranged in the respective basic fixture is bridged does not exceed a limit number above 0.

This can make it possible, for example, to maintain ongoing operation or emergency operation of the medical device even if, for example, one of the battery modules arranged in the basic fixtures fails and has to be bridged. At the time of failure of the aforementioned battery module, for example, no battery module may yet be arranged in the additional fixture. Nevertheless, ongoing operation or emergency operation is still possible. At a later time, a battery module can be plugged into the additional fixture and the charge levels can be equalized. While the basic charge level and the additional charge level are being equalized, the battery module arranged in the additional fixture is usually not involved in the ongoing operation or emergency operation of the medical device. During this period, however, the ongoing operation or emergency operation of the medical device can be maintained. After equalization of the charge levels, the battery module arranged in the additional fixture can either be removed from the additional fixture and inserted into a free basic fixture or integrated into the network of battery modules while retaining its arrangement in the additional fixture.

According to FIG. 1, a (in principle, any) medical device 1 is operated electrically. The medical device 1 therefore has a number of electrical loads 2. The medical device 1 is usually supplied with electrical energy via an input stage 3 from a supply network 4. According to FIG. 1, there is an intermediate circuit 5 to which the input stage 3 and output stages 6, via which the loads 2 are supplied with electrical energy, are connected. The embodiment with the intermediate circuit 5 is customary, but not mandatory. The medical device 1 can be embodied as an X-ray system, for example.

The medical device 1 also has an electric battery storage system 7. The battery storage system 7 supports and/or enables the ongoing operation of the medical device 1 (i.e. operation when supplied via the supply network 4). Alternatively or in addition, the battery storage system 7 can also be used to enable emergency operation of the medical device 1 (i.e. operation when not supplied via the supply network 4). The battery storage system 7 can, for example, be connected to the intermediate circuit 5 via a converter circuit 8.

Figure 2:
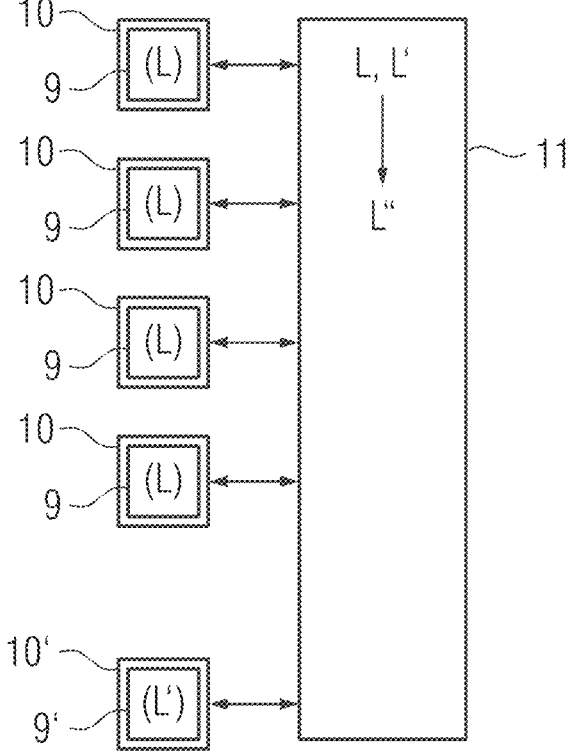
FIG. 2 illustrates a battery storage system according to one or more example embodiments.

According to FIG. 2, the battery storage system 7 has a plurality of battery modules 9, 9'. In FIG. 2 as well as the other figures, five battery modules 9, 9' are always shown. However, the number of battery modules 9, 9' can be greater or smaller. As a minimum, however, three battery modules 9, 9' are present.

The battery modules 9, 9' are arranged in module fixtures 10, 10'. The module fixtures 10, 10' serve at least to mechanically accommodate the battery modules 9, 9'. If necessary, they can also realize the electrical integration of the battery modules 9, 9' into the medical device 1. Regardless of whether the module fixtures 10, 10' also realize the electrical integration of the battery modules 9, 9' into the medical device 1 or whether this takes place independently (for example, via cables with pre-assembled plugs at their ends), a power-related interconnection of the battery modules 9, 9' is determined by the arrangement of the battery modules 9, 9' in the module fixtures 10, 10'.

The module fixtures 10, 10' comprise several similar module fixtures 10, hereinafter referred to as basic fixtures 10. The battery modules 9 arranged in the basic fixtures 10 are referred to hereinafter as basic modules 9. Furthermore, the module fixtures 10, 10' comprise at least one further module fixture 10', hereinafter referred to as an additional fixture 10'. The battery modules 9' arranged in the additional fixtures 10' are referred to hereinafter as additional modules 9'.

Hereinafter, it is assumed that there is only a single additional fixture 10', even if several additional fixtures 10' could be present. Due to the fact that in the present case— even if only by way of example—a total of five battery modules 9, 9' is always assumed, there are consequently four basic fixtures 10.

The battery modules 9, 9' each have a charge level L, L'. The respective charge level L, L' may vary between 0 (=fully discharged) and 1 (=fully charged). The charge level L of the basic modules 9 is uniform and is referred to hereinafter as the basic charge level L. The charge level L' of the additional module 9'—hereinafter referred to as the additional charge level L'—is independent of the basic charge level L. It can therefore have the same value, but it can also have a different value from the basic charge level L.

An equalizing arrangement 11 is assigned to the battery storage system 7. The equalizing arrangement 11 is capable of effecting a low-loss equalization of the basic charge level L and the additional charge level L' between the basic modules 9 on the one hand and the additional module 9' on the other hand. The equalizing arrangement 11 can therefore have the effect that, after equalization with one another, the basic charge level and the additional charge level L' have the same value, i.e. a uniform charge level L" for all battery modules 9, 9'. However, the equalizing arrangement 11 is also limited to this functionality. In particular, it is not capable of bringing about a uniform basic charge level L, L' within the basic modules 9 or within a single basic module 9 or even within a single additional module 9'. Rather, this must be provided from the outset. Possible embodiments of the equalizing arrangement 11 are explained hereinafter in connection with the other figures.

Figure 3:
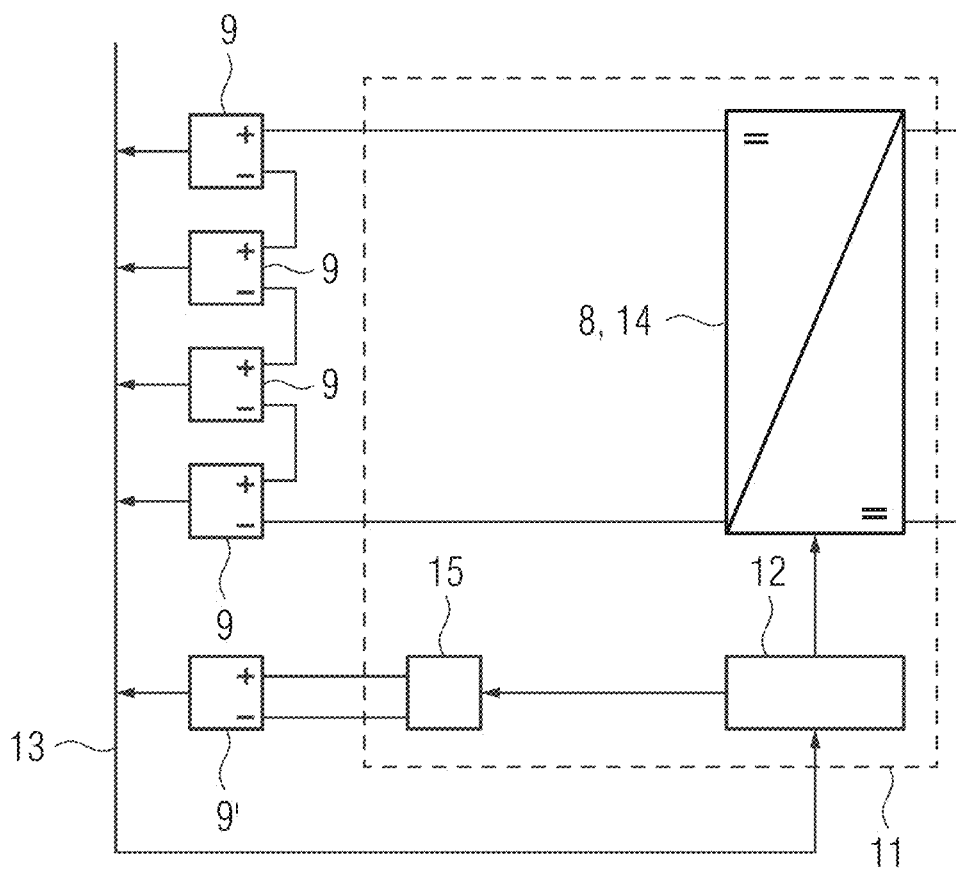
FIG. 3 illustrates a battery storage system and an equalizing arrangement according to one or more example embodiments.

According to FIG. 3, the equalizing arrangement 11 comprises a battery management system 12 of the medical device 1. Such a battery management system 12 is customary and therefore need not be explained in more detail. The battery modules 9, 9'—the module fixtures 10, 10' are not shown in FIG. 3—are connected via a communication link 13—as a rule, a serial bus—connected to the battery management system 12 by a data-related interconnection (e.g., a connection to at least transmit data from the modules 9, 9' to the battery management system 12). The battery modules 9, 9' are therefore capable of transmitting their respective charge level L, L' to the battery management system 12.

In the simplest case, which is not shown in FIG. 3, the additional module 10' is not connected at all in terms of power but is only connected to the battery management system 12 by a data-related interconnection via the communication link 13. In this case, as a matter of principle, charging and discharging of the battery storage system 7 affect only the basic modules 9. In this case, the equalization of the basic charge level L and the additional charge level L' with one another is brought about exclusively by charging and discharging the basic modules 9. In this case, the equalizing arrangement 11 has a basic charging device 14. The battery management system 12 determines a control for the basic charging device 14 by first determining a target value for the basic charge level L on the basis of the additional charge level L' and then determining the control on the basis of the deviation of the basic charge level L from the target value for the basic charge level.

For this purpose, a basic charging device 14 spanning the basic fixtures 10 can be assigned to the basic fixtures 10, via which the uniform basic charge level L can be changed. Due to the fact that the additional module 9' is not connected in terms of power, this change to the uniform basic charge level L takes place without influencing the additional charge level L'. The basic charging device 14 can, for example, be identical to the converter circuit 8, via which energy is exchanged with the intermediate circuit 5.

During normal operation of the medical device 1, i.e. if the supply of electrical energy via the input stage 3 and the supply network 4 is possible, in principle the battery storage system 7 can be operated in the same manner to equalize the uniform basic charge level L to the additional charge level L' as if the additional module 9' were not present, i.e. the additional module 9' were not arranged in the additional fixture 10'. In this case, the battery management system 12 merely ensures that the required adjustment of the basic charge level L takes place. Therefore, if the basic charge level L is lower than the additional charge level L', only the energy drawn from the battery storage system 7 is slightly reduced and/or the energy supply to the battery storage system 7 is slightly increased until the basic charge level L is adjusted to the additional charge level L'. Conversely, if the basic charge level L is greater than the additional charge level L', only the energy supply from the battery storage system 7 is slightly increased and/or the energy supply to the battery storage system 7 is slightly reduced until the basic charge level L is adjusted to the additional charge level L'.

During emergency operation of the medical device 1, i.e. if the supply of electrical energy via the input stage 3 and the supply network 4 is not possible, all the electrical energy must be drawn from the battery storage system 7 in order to maintain emergency operation. In this case too, however, a similar approach can be taken with regard to the discharging of the basic modules 9.

In accordance with the representation in FIG. 3, the equalizing arrangement 11 has an additional charging device 15 which is proprietarily assigned to the additional fixture 10'. The additional charge level L' of the additional module 9' can be changed via the additional charging device 15. The additional charging device 15 acts exclusively on the additional module 9'. Charging and discharging of the additional module 9' therefore takes place without influencing the uniform basic charge level L of the basic module 9.

It is possible that the equalization of the basic charge level L and the additional charge level L' with one another is only achieved by the charging and discharging of the additional module 9'. In this case, the battery management system 12 determines a control for the additional charging device 15 by first determining a target value for the additional charge level L' based on the basic charge level L and then ascertaining the control based on the deviation of the additional charge level L' from the target value for the additional charge level L'.

However, it is also possible that the additional charging device 15 is present in addition to the basic charging device 14. In this case, the charge levels L, L' can be changed in opposite directions in order to equalize the basic charge level L and the additional charge level L'. In this case, the two approaches mentioned above are combined with one another.

Figure 4:
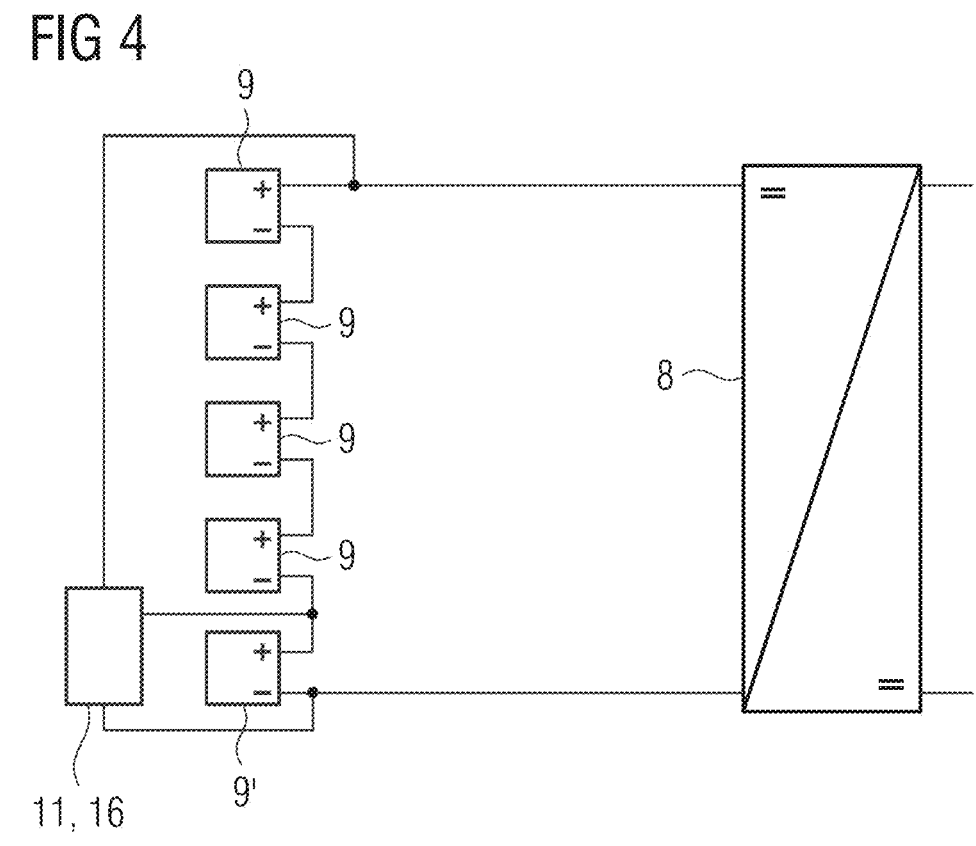
FIG. 4 illustrates a battery storage system and an equalizing arrangement according to one or more example embodiments.

FIG. 4 shows an alternative to the embodiment of FIG. 3. The module fixtures 10, 10' are also not shown in FIG. 4. According to FIG. 4, an active balancing circuit 16 is assigned to the battery storage system 7. Via the active balancing circuit 16, charge can be transferred with low loss between all of the basic modules 9 on the one hand and the additional module 9' on the other hand. In doing so, the change in the additional charge level L' is distributed evenly across the basic modules 9. For example, if the additional charge level L' is increased by x, the basic charge level L of the basic modules 9 is correspondingly reduced evenly by y, wherein the reduction in the basic charge level L of an individual basic module 9 causes an increase in the additional charge level L' n x/4. The "4" results in the present case because it is assumed that there are four basic modules 9.

FIG. 3 shows an embodiment in which the additional module 9' is not involved in the operation of the basic module 9 in terms of power. Such non-integration is also possible in the embodiment of FIG. 4. If the additional module 9' is not involved in the operation of the basic modules 9 in terms of power, during ongoing operation and/or during emergency operation of the medical device 1 electrical energy is drawn from the basic modules 9 but not from the additional module 9' in order to operate the medical device 1. However, it is also possible that during ongoing operation and/or emergency operation of the medical device 1, electrical energy is drawn both from the basic modules 9 and from the additional module 9' in order to operate the medical device 1. In particular, this is possible in connection with the embodiment according to FIG. 4 because the active balancing circuit 16 can also equalize the charge levels L, L' during ongoing operation of the battery storage system 7. However, FIG. 3 can also be modified accordingly.

It is even possible to dynamically involve or not involve the additional module 9' in the operation of the basic modules 9 in terms of power as required. A possible embodiment for this is explained hereinafter in connection with FIG. 5.

Figure 5:
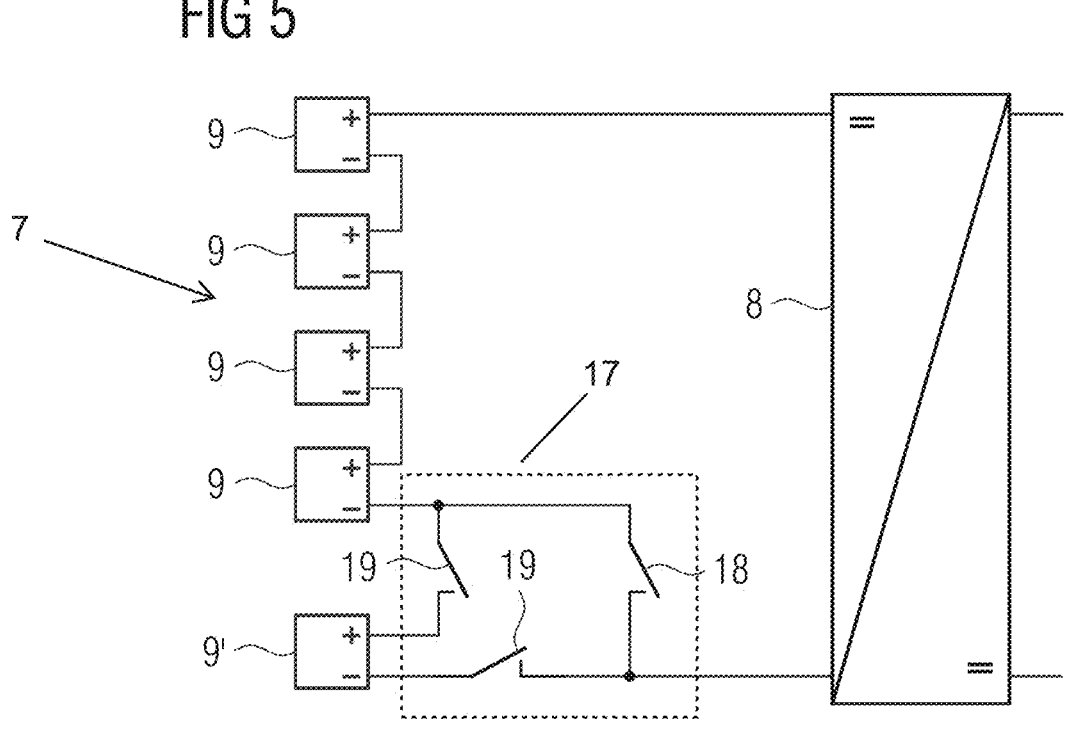
FIG. 5 illustrates a battery storage system and an equalizing arrangement according to one or more example embodiments.

According to FIG. 5, a switching facility 17 is assigned to the battery storage system 7. The switching facility 17 comprises at least the switch 18 and one of the two switches 19, preferably the switch 18 and both switches 19. The switches 18, 19 are preferably electronic switches (for example, IGBTs or MOSFETs) which can be switched so quickly that the operation of the medical device 1 is not interrupted. The switching times of the switches 18, 19 can be in the ms range or even in the μs or ns range as required.

In some cases, it may also be possible for the switches 18, 19 to be designed as electromechanical or even as manually actuated switches (such as, for example, manually plugged-in switching bridges).

In many cases, the switching facility 17 can be controlled by the battery management system 12. Here, the switches 18 and 19 are switched in push-pull mode by the battery management system 12. If the switch 18 is closed, the switch 19 is open or the switches 19 are open. In this state, the additional module 9' is not involved in the operation of the basic modules 9 in terms of power. Conversely, if the switch 18 is open, the switch 19 is closed or the switches 19 are closed. In this state, the additional module 9' is involved in the operation of the basic modules 9 in terms of power.

Thus, it is easy to dynamically adjust whether electrical energy is drawn exclusively from the basic modules 9 or both from the basic modules 9 and the additional module 9' during ongoing operation and/or during emergency operation of the medical device 1 in order to operate the medical device 1. The opposite approach is also possible, i.e. it is possible to dynamically adjust whether electrical energy is supplied exclusively to the basic modules 9 or both to the basic modules 9 and to the additional module 9' during ongoing operation of the medical device 1.

The module fixtures 10, 10' are also not shown in FIG. 5.

Figure 6:
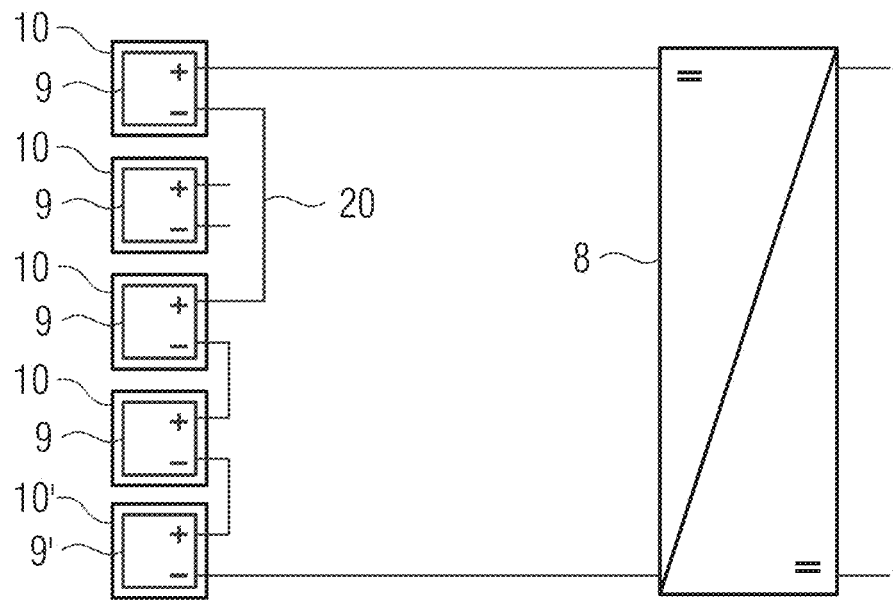
FIG. 6 illustrates a battery storage system.

The battery storage system 7 is preferably designed in such a way that it supports and/or enables the ongoing operation of the medical device 1 and/or enables the emergency operation of the medical device 1 even if a number of basic fixtures 10 in which no battery module 9 is arranged or in which the battery module 9 arranged in the respective basic fixture 10 is bridged does not exceed a limit number. The limit number can be 1 or 2, for example. FIG. 6 shows an embodiment of the battery storage system 7 in which one of the basic modules 9 is bridged via a switching bridge 20, for example. This basic module 9 is decoupled from the power network of the battery modules 9, 9'. The switching bridge 20 acts analogously to the switching facility 17. It therefore does not short-circuit the corresponding basic module 9. The switching bridge 20 can be manually operated (for example, plugged in) in particular by an operator (not shown). In individual cases, however, it can also be designed as an electromechanical or electronic switch.

It is possible that, in the event that one (or more) of the basic modules 9 is not present or is bridged, the operation of the battery storage system 7 is only possible in accordance with the illustration in FIG. 6 if the additional module 9' is present and is integrated into the power network of the remaining basic modules 9. However, it is also possible that the operation of the battery storage system 7 is also possible in such a case if the additional module 9' is not present or is not integrated into the power network of the remaining basic modules 9.

Example embodiments have many advantages. In particular, the energy-efficient integration of an additional battery module 9' with any charge level L' into a battery storage system 7 which already has several battery modules 9 with a uniform charge level L is possible in a simple and cost-effective manner. It is possible to replace a single battery module 9, 9'. The entire battery storage system 7 therefore does not need to be replaced. The time required to carry out the charge equalization is significantly reduced compared to the procedures of the prior art.

Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a Graphics Processing Unit (GPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A medical device comprising:
an electric battery storage system including a plurality of battery modules;
module fixtures, wherein
the plurality of battery modules are in the module fixtures,
an arrangement of the plurality of battery modules in the module fixtures provide a power-related interconnection of the plurality of battery modules, and
the module fixtures are divided into a plurality of basic fixtures and at least one additional fixture; and
an equalizing arrangement assigned to the electric battery storage system, the equalizing arrangement being configured to equalize a low-loss equalization of a basic charge level and an additional charge level between battery modules in the plurality of basic fixtures and a battery module in the additional fixture, each of the battery modules in the plurality of basic fixtures having a uniform basic charge level and the battery module in the additional fixture having an additional charge level, and the equalizing arrangement not being configured to cause the uniform basic charge level within the battery modules in the basic fixtures.

2. The medical device of claim 1, further comprising:
a battery management system, wherein
the plurality of battery modules are connected to the battery management system by a data-related interconnection such that the plurality of battery modules are configured to transmit their respective charge level to the battery management system, and
the basic fixtures are assigned a basic charging device spanning the basic fixtures and via which the uniform basic charge level of the battery modules in the basic fixtures is changeable without influencing the additional charge level of the battery module in the additional fixture.

3. The medical device of claim 2, wherein
in order to adjust the uniform basic charge level of the battery modules in the basic fixtures to the additional charge level of the battery module in the additional fixture during an ongoing operation of the medical device, the battery modules in the basic fixtures are discharged or electrical energy is supplied to the battery modules in the basic fixtures in a same manner as if no battery module were in the additional fixture, and
in an emergency operation of the medical device and in order to adapt the uniform basic charge level of the battery modules in the basic fixtures to the additional charge level of the battery module in the additional fixture, discharging of the battery modules in the basic fixtures is carried out in the same manner as if no battery module were in the additional fixture.

4. The medical device of claim 2, wherein the additional fixture is proprietarily assigned an additional charging device, the additional charging device is configured to change the additional charge level of the battery module in the additional fixture without influencing the uniform basic charge level of the battery modules in the basic fixtures.

5. The medical device of claim 1, further comprising:
a battery management system, wherein
   the plurality of battery modules in the module fixtures are connected by a data-related interconnection to the battery management system such that the plurality of battery modules in the module fixtures are configured to transmit their respective charge level to the battery management system, and
   the additional fixture is proprietarily assigned an additional charging device, the additional charging device is configure to change the additional charge level of the battery module in the additional fixture without influencing the uniform basic charge level of the battery modules in the basic fixtures.

6. The medical device of claim 1, further comprising:
an active balancing circuit assigned to the electric battery storage system, the active balancing circuit configured to transfer charge with low loss between all of the battery modules in the basic fixtures and the battery module in the additional fixture, and such that a change in the additional charge level of the battery module in the additional fixture is distributed evenly across the battery modules in the basic fixtures.

7. The medical device of claim 1, wherein during at least one of an ongoing operation or an emergency operation of the medical device, the medical device is configured to draw electrical energy from the battery modules in the basic fixtures for operating the medical device and not from the battery module in the additional fixture.

8. The medical device of claim 1, wherein during at least one of an ongoing operation or an emergency operation of the medical device, the medical device is configured to draw electrical energy from the battery modules in the basic fixtures and from the battery module in the additional fixture.

9. The medical device of claim 1, further comprising:
a switching facility assigned to the electric battery storage system, the electric battery storage system is configured to dynamically adjust whether electrical energy is drawn exclusively from the battery modules in the basic fixtures or is drawn both from the battery modules in the basic fixtures and from the battery module in the additional fixture during at least one of an ongoing operation or an emergency operation of the medical device.

10. The medical device of claim 1, wherein at least one of,
the electric battery storage system is configured to at least one of support or enable an ongoing operation of the medical device, or
the electric battery storage system is configured to enable an emergency operation of the medical device as long as a number of basic fixtures in which no battery module is arranged or in which the battery module in a respective basic fixture is bridged does not exceed a limit number above 0.

11. The medical device of claim 3, wherein the additional fixture is proprietarily assigned an additional charging device, the additional charging device is configured to change the additional charge level of the battery module in the additional fixture without influencing the uniform basic charge level of the battery modules in the basic fixtures.

12. The medical device of claim 2, wherein during at least one of an ongoing operation or an emergency operation of the medical device, the medical device is configured to draw electrical energy from the battery modules in the basic fixtures for operating the medical device and not from the battery module in the additional fixture.

13. The medical device of claim 2, wherein during at least one of an ongoing operation or an emergency operation of the medical device, the medical device is configured to draw electrical energy from the battery modules in the basic fixtures and from the battery module in the additional fixture.

14. The medical device of claim 2, further comprising:
a switching facility assigned to the electric battery storage system, the electric battery storage system is configured to dynamically adjust whether electrical energy is drawn exclusively from the battery modules in the basic fixtures or is drawn both from the battery modules in the basic fixtures and from the battery module in the additional fixture during at least one of an ongoing operation or an emergency operation of the medical device.

15. The medical device of claim 2, wherein at least one of,
the electric battery storage system is configured to at least one of support or enable an ongoing operation of the medical device, or
the electric battery storage system is configured to enable an emergency operation of the medical device as long as a number of basic fixtures in which no battery module is arranged or in which the battery module in a respective basic fixture is bridged does not exceed a limit number above 0.

* * * * *